United States Patent [19]

Purzycki et al.

[11] Patent Number: 4,666,671

[45] Date of Patent: May 19, 1987

[54] METHOD FOR DEODORIZING URINALS AND TOILET BOWLS WITH FRAGRANCED GEL BLOCKS

[75] Inventors: Kenneth L. Purzycki, Lake Parsippany; Peter C. Ryan, Westfield, both of N.J.; Anthony J. Leardi, Middletown, N.Y.

[73] Assignee: Givaudan Corporation, Clifton, N.J.

[21] Appl. No.: 719,178

[22] Filed: Apr. 3, 1985

[51] Int. Cl.$^4$ ................................................. A61L 2/16
[52] U.S. Cl. ............................................. 422/5; 4/228; 252/522 R; 424/76
[58] Field of Search ............... 422/5; 4/222, 228, 231; 252/522 R; 424/76

[56] References Cited

U.S. PATENT DOCUMENTS

| | | | |
|---|---|---|---|
| 3,767,787 | 10/1973 | Segal | 424/76 |
| 3,902,022 | 9/1975 | Ohara et al. | |
| 3,943,243 | 3/1976 | Kook | |
| 4,056,612 | 11/1977 | Lin | 424/76 |
| 4,067,824 | 1/1978 | Teng et al. | 424/76 |
| 4,096,593 | 6/1978 | Vlahakis | |
| 4,107,289 | 8/1978 | Kaufman | 424/76 |
| 4,125,478 | 11/1978 | Sullivan et al. | 424/76 |
| 4,149,986 | 4/1979 | Dickson | |
| 4,178,264 | 12/1979 | Streit et al. | 422/5 |
| 4,209,864 | 7/1980 | Lindauer | 4/222 |
| 4,250,165 | 2/1981 | Foley | |
| 4,320,873 | 3/1982 | Martens, III et al. | |
| 4,511,552 | 4/1985 | Cox | 424/76 |

FOREIGN PATENT DOCUMENTS

| | | |
|---|---|---|
| 2162790 | 7/1972 | Fed. Rep. of Germany . |
| 2407947 | 9/1974 | Fed. Rep. of Germany . |
| 2907029 | 2/1979 | Fed. Rep. of Germany . |
| 50-24449 | 3/1975 | Japan . |

Primary Examiner—David L. Lacey
Attorney, Agent, or Firm—Robert F. Tavares

[57] ABSTRACT

This invention provides new and improved urinal blocks and toilet bowl rim blocks which are fragranced gels and which can be used to control the release of germicides, deodorants, cleaning agents, dyes and/or other releasable "active ingredients" into a toilet system for the purpose of sanitizing, cleaning and/or deodorizing.

7 Claims, No Drawings

METHOD FOR DEODORIZING URINALS AND TOILET BOWLS WITH FRAGRANCED GEL BLOCKS

BACKGROUND OF THE INVENTION

There has been a trend during the past few years to provide products that will sanitize, clean and/or deodorize lavatory fixtures such as toilet bowls and urinals as they are used. All of these products involve some system of a sustained and controlled release of the active ingredient (germicide, cleaning agent, deodorant, etc.) into the toilet bowl or urinal each time that the fixture is used and/or flushed.

Commonly used are so-called rim blocks or urinal blocks, which are manufactured by compressing or melting sublimable material, such as para-dichlorobenzene, camphor, naphthalene and adamantane into blocks. Examples of such systems are disclosed in U.S. Pat. Nos. 3,943,243, 3,903,022 and Japanese Pat. No. 75 24,449. These systems have certain limitations. Their effective life span depends on the rate of sublimation rather than on use. Sublimable blocks, which are formed by compression, are also limited as to the amount of active ingredients (germicides, surfactants, fragrance, etc.) they can hold. Attempts to incorporate higher levels of such ingredients usually fail either because such ingredients tend to be pressed out during manufacture or because soft, crumbly blocks are produced. Sublimable materials also have characteristic odors. In order to cover these odors, fragrance selection is limited to extremely strong fragrance compounds which may not be that desirable from an olfactory point of view. There is also some concern with the fact that the block material itself sublimes into the room and is inhaled along with the fragrance. For example, para-dichlorobenzene is currently the subject of environmental concern and its use for purposes wherein the possibility exists for human exposure may be restricted in the future.

Other solid toilet system sanitizers, cleaners and deodorizers have been manufactured by compressing granular or powder mixtures of surfactants, hydratable salts, (e.g., $Na_2SO_4$, $NaHSO_4$, $Na_2B_4O_7$, $NaP_2O_7$, $MgSO_4$, etc.) and other additives where desired (e.g. dyes, perfumes, and/or other minor components) or by cooling a molten mixture of the above ingredients. See, for example, German Pat. Nos. 2,162,790, 2,407,947, 2,907,029 and U.S. Pat. Nos. 4,149,986, 4,096,593 and the references cited therein. Such molded surfactant blocks suffer from many of the same drawbacks and limitations mentioned for the sublimable blocks. The action of flushing or other turbulence that is required to release the active ingredients often causes the block to soften and crumble. It is also known that surfactants suppress the rate of evaporation of volatile materials such as fragrances. (U.S. Pat. Nos. 4,250,165 and 4,320,873 and the references cited therein.) Surfactant blocks do not, therefore, release their volatile components (e.g. fragrance components) as well as sublimable blocks, and have been found to be inferior to the sublimable blocks for deodorizing toilet bowls and urinals.

A need exists for a product which would deodorize like a sublimable block, release other active ingredients, germicides, surfactants, etc., upon demand like a molded surfactant block, and which would release the fragrance material into the surrounding area over a long period of time without at the same time releasing undesirable products into the air or water. This invention provides such a product.

THE INVENTION

It is the surprising and unexpected finding of this invention that a solid gel system, which is prepared from materials which have significant water solubility, can be used as the vehicle to uniformly and consistently release, over a period of time, active ingredients that will sanitize and/or deodorize a toilet bowl or urinal. It is also surprising and unexpected that such a solid gel system can survive the turbulence of repeated flushing and exposure to urine without rapid dissolution or deterioration, and maintains the ability to release active ingredients, including fragrances, for a sustained period of four to five weeks. The sanitizing and cleaning agents are dispersed on demand by the flushing action, while the fragrance used to deodorize the system is continually emitted by evaporation. In addition, the preferred gels of this invention can be formulated so as to contain higher levels of active ingredients, including fragrances, than is possible with either the molded surfactant or sublimable blocks mentioned earlier.

The solid gel urinal and toilet bowl rim blocks of this invention have several advantages over the sublimable blocks or the molded surfactant blocks described in the prior art. The gels of this invention can perform for up to thirty days or longer continuously emitting a pleasant fragrance while at the same time releasing other active ingredients into the toilet bowl or urinal. Another advantage is that the fragrance used need not be overwhelming in order to cover over undesirable odors due to volatile materials such as para-dichlorobenzene. The fragrance used can provide a delicate and pleasant odor more suitable and desirable for the lavatory or bathroom. A third advantage is that the release of the fragrance and the other active ingredients is controlled and quite linear over about thirty days and there is no rapid decline of effectiveness with time.

DESCRIPTION OF THE PREFERRED EMBODIMENTS

The reason that solid gels can be used as disclosed in this invention for deodorizing urinals and toilet bowls is the surprising and unexpected finding that these gels survive intact for a long time, thirty days or longer, despite their exposure to urine and repeated flushings. It is recognized by one of ordinary skill in the art that there are a number of different formulations for making solid gels. Ingredients which are common to most of these formulations are gelling agents, solvents or solvent mixtures, and water. The preferred gel is one that will be solid and somewhat rigid, will melt high enough to maintain its integrity and not soften if the temperature rises during storage, and will hold enough of the fragrance and/or other active materials to provide sufficient odor and/or activity over the period of use.

The gels preferred to be used in this invention include a gelling agent, water, an organic solvent containing one or more hydroxyl groups and a fragrance material. The relative amounts of the ingredients will normally depend on the level of fragrance used and the physical properties desired in the final product.

The gelling agents which can be employed in the gel of this invention are exemplified by, but not limited to, sodium salts of fatty acids containing ten to twenty carbon atoms (for example sodium stearate), sodium alginate, carboxy methyl cellulose, carrageenan, hydroxypropyl cellulose, starches and gums. Sodium stearate is especially preferred because it is very economical and is compatible with a wide range of solvents. Sodium stearate gels have been particularly successful in the practice of this invention.

The gelling agents should be employed in a range of 2% to 20% by weight of the gel to achieve a suitable degree of hardness. The amount used in the formulations is, of course, determined by such factors as the nature of the gelling agent (or combination of gelling agents) being used and the nature and amounts of the additional components. It would be well within the skill of the ordinary practitioner to determine the optimal amount of gelling agent required. Sodium stearate is preferably used in an amount that is 3% to 10% by weight of the gel. In most cases, if less than 3% is used the gel may not attain the desired hardness. Amounts above 10% do not appear to offer any advantage for purposes of the present invention. Since it is more economical to use lesser amounts of sodium stearate, it is preferred to use no more than is necessary to achieve the desired hardness.

Suitable organic solvents for preparing the gels of this invention are preferably solvents having one or more hydroxyl groups, e.g. an alkyl alcohol having one to six carbon atoms, alkyl diol having two to seven carbon atoms or alkyl ether alcohol having three to eight carbon atoms which have one hydroxyl group and one or two ether linkages. A combination of solvents may be employed in formulating the gel if desired.

The alkyl alcohols are exemplified by, but not limited to, methanol, ethanol, 1-propanol, 2-propanol, butanol, pentanol and the like. The preferred alkyl alcohol is 2-propanol because it has an acceptable flash point, is not toxic and has an acceptably weak odor.

The alkyl diols are exemplified by, but not limited to, ethylene glycol, propylene glycol, hexylene glycol (2-methyl-2,4-pentanediol), di-1,2-propylene glycol, and the like. The preferred alkyl diols are those which have the ability to increase the rigidity and melting point. Hexylene glycol is especially preferred.

The alkyl ether alcohols which can be used are exemplified by, but not limited to, 2-methoxyethanol, 2-ethoxyethanol, 2-butoxyethanol, 2-(2-methoxyethoxy)ethanol, 2-(2-ethoxyethoxy)ethanol and 2-(2-butoxyethoxy)ethanol. The preferred alkyl ether alcohols are those which contribute the least odor, but act as a co-solvent for the active ingredients in the gel. The preferred alkyl ether alcohol is 2-(2-ethoxyethoxy)ethanol.

The amount of solvent will usually depend on the amount of other ingredients in the gel, i.e. the amount of fragrance desired, the amount of gelling agent, the amount of water plus any other active ingredients that may be desired. A range of 30% to 80% solvent would be suitable with a range of 40% to 80% being preferred.

The fragrance in the gel of this invention can be any conventional commercially available perfume oil. These are complex mixtures of volatile compounds including: esters, ethers, aldehydes, alcohols, unsaturated hydrocarbons, terpenes and other ingredients which are well known to those skilled in the art of perfumery. Their use as to type and proportion is limited only by their compatability and preference in the gel matrix. It is one of the advantages of this invention that a wide variety of fragrance components are compatible with the gel system and one can choose from a wide variety of fragrances.

The fragrance may be present in an amount from 1% to 55% by weight of the gel. It is preferred for most applications to use an amount in the range of 10% to 40%. The amount of fragrance used will often depend on the type of the fragrance, the size of the area to be deodorized per unit, the period over which the fragrance should be released and other more subjective factors such as user preference.

Water is employed in the gel of this invention in a suitable range of from about 2% to 10% by weight of the gel for most gels. The presence of water has been found to stabilize the gel and prevent an undesirable cloudiness. (The clarity of the gel is a good indication that the gel is a uniform colloid. Cloudiness usually indicates a precipitation of one or more of the components.) Except in the cases of water gels (e.g. gels where carrageenan or carboxy methyl cellulose are used) amounts above 10% are unnecessary since there is no further contribution to be made to the transparency of the gel and the additional water normally has an adverse effect on the hardness of the gel. (The water gels are less preferred since they do not hold as much fragrance and normally do not last as long as those gels wherein less water is used, e.g. those wherein sodium stearate is used as the gelling agent.) When sodium stearate is used, 5% to 10% water is preferred.

The other active ingredients of this invention are those which are commercially available, such as germicides, surfactants and preservatives and are used at the levels recommended by the supplier to achieve the intended results.

While a suitable gel would be any gel that is solid at room temperature, it is preferred to formulate the gel so that the product melts above 120° F. (Gels do not have a sharp melting point, but melt over a range. Any reference to a gel melting above a certain temperature is intended to mean that it begins to melt above that temperature.) A higher melting gel is preferred so that it may withstand temperatures in warmer climates and can be stored at these temperatures. It is especially preferred that the gel melt above 130° F. particularly somewhere in the range between 130° F. to 200° F. In general it has been found that an increase in the amount of gelling agent and/or an increase in the amount of solvent increases the temperature at which the gel melts. The amount of increase obtained is, of course, dependent on the particular component being adjusted.

The preferred procedures for preparing the gel will depend on the kind of gel being made. Most of these procedures are known in the art and depend, for the most part, on the particular gelling agent being used. In some cases, carrageenan for instance, high shear mixing is required. For other gelling agents, certain temperatures may be required.

When the gelling agent is the especially preferred sodium stearate, it is preferred to mix the gelling agent, water and solvent at 80°–85° C. until a clear solution is obtained. Then the temperature is reduced and the fragrance is added. Other additives, when desired, may be added separately or along with either the fragrance or the mixture of the gelling agent, solvent and water. The nature of such additives will determine which of the methods of addition is preferred. (Alternatively a portion of the solvent may be added along with the fragrance and/or the additives.) The resulting solution is then poured into a mold and allowed to cool and gel.

The gel can be molded directly into containers, or molded separately into any desired shape, preferably a stick or rod shape which can be placed in a separate container. The amount of gel used will, of course, depend on the frequency of use expected and on the length of time before the gel article is to be replaced. For most applications in urinals or toilet bowls, about 25 to 75 grams of gel is suitable.

A preferred container for toilet bowls will divert a portion of the flush water and allow a portion to come in contact with the gel. There should also be provision for the active ingredients to escape. The container can be manufactured out of any suitable material and should provide a holding device which positions the container under the rim in the stream of flushing water.

For urinals the gel should preferably be molded into a cup and the cup-like device placed in an inverted position in the urinal. The container should be above the water level so that the fragrance material can escape into the air and deodorize the surrounding area.

ILLUSTRATION OF THE PREFERRED EMBODIMENTS

The following examples are for the purpose of illustration only and are in no way to be considered as limiting. Various changes and modifications in the gel formulations disclosed herein will occur to those skilled in the art and to the extent that such changes and modifications are embraced by the claims, they are to be understood as constituting part of the present invention.

Melting ranges were determined in the following manner. The gel was placed in a Pyrex ® test tube (4"×0.5" I.D.) heated in a Silicone oil bath at a rate of 0.5° per minute. The melting range was taken from first appearance of liquid to complete melt.

EXAMPLE 1

This example illustrates a gel typical of those contemplated by the invention.

| Component[a] | |
|---|---|
| Part A | |
| Water | 7.0% |
| 2-(2-Ethoxyethoxy)ethanol[b] | 10.0% |
| Sodium Stearate | 8.0% |
| Part B | |
| 2-Propanol | 50.0% |
| Fragrance | 25.0% |
| | 100.0% |

[a]Percent by weight
[b]Available under the name Carbitol ® from Union Carbide

Part A is mixed and heated at 80°–85° C., with stirring at moderate speed until the solution is clear. The temperature is reduced to 75° C., and part B, premixed, is added while maintaining the temperature at 65°–75° C. The resulting solution is poured into molds and allowed to cool. Gelling starts to occur at 55°–60° C. Melting Range: 142°–158° F.

Sixty-gram samples of the above gel were placed in urinals and were found by a panel of eight professional fragrance evaluators to effectively deodorize the system throughout a four-week period without a notable decrease in effectiveness.

EXAMPLE 2

This example illustrates a gel typical of those contemplated by the invention.

| Component[a] | |
|---|---|
| Part A | |
| Water | 5.0% |
| 2-(2-Ethoxyethoxy)ethanol | 34.0% |
| Sodium Stearate | 4.0% |
| Part B | |
| 2-Propanol | 20.0% |
| Fragrance | 35.0% |
| Germicide | 2.0% |
| | 100.0% |

[a]Percent by weight

Part A is mixed and heated at 80°–85° C., with stirring at moderate speed until the solution is clear. The temperature is reduced to 55° C., and part B, premixed, is added while maintaining the temperature at 55° C. The resulting solution is poured into molds and allowed to cool. Gelling starts to occur at 40°–45° C. Melting Range: 125°–145° F.

The above gel was place in a urinal for a four-week test period and was found to effectively deodorize the system.

EXAMPLE 3

This example illustrates other formulas contemplated by this invention.

| Component[a,b] | I | II |
|---|---|---|
| Part A | | |
| Water | 9.0% | 10.0% |
| Hexylene Glycol | 10.0% | 14.0% |
| Sodium Stearate | 8.5% | 8.5% |
| Part B | | |
| 2-Propanol | 57.0% | 57.0% |
| Fragrance | 15.0% | 10.0% |
| Germicide | 0.5% | 0.5% |
| Melting Range (°F.) | 162°–176° | 153°–174° |

[a]Percent by weight
[b]The gels were prepared in a manner similar to Examples 1 and 2.

EXAMPLE 4

This example illustrates how a change in solvent can affect the melting range of the gel. The solvents utilized and the resultant melting ranges are given in Table 1. The procedure of Examples 1 and 2 was followed. The sodium stearate was dissolved in the water and solvent and the fragrance was added separately.

| Component | Percent By Weight |
|---|---|
| Part A | |
| Water | 5% |
| Solvent | 64% |
| Sodium Stearate | 6% |
| Part B | |
| Fragrance | 25% |
| | 100% |

TABLE 1

| Solvent | Melting Range (°F.) |
|---|---|
| Methanol | 125°–133° |
| Isopropanol | 131°–181° |
| N—Butanol | 140°–156° |
| N—Hexanol | 135°–142° |
| Mixture of C-12 to C-15 alcohols[a] | 77°–136° |
| Propylene glycol | 77°–120° |
| Ethylene glycol | 77°–140° |

TABLE 1-continued

| Solvent | Melting Range (°F.) |
|---|---|
| Hexylene glycol | 187°–194° |
| 2-(2-Ethoxyethoxy)ethanol | 113°–122° |

*Available under the name Neodol ® from Shell Oil Co.

In each instance a gel of suitable hardness at room temperature was obtained.

EXAMPLE 5

This example illustrates the effect that varying the amounts of the gelling agent and the solvent composition can have on the melting range of the gel.

| Component$^{a,b}$ | I | II | III | IV | V | VI | VII | VIII |
|---|---|---|---|---|---|---|---|---|
| Part A | | | | | | | | |
| Sodium Stearate | 5% | 6% | 5% | 6% | 5% | 6% | 5% | 6% |
| 2-(2-Ethoxy-ethoxy)-ethanol | 28% | 27% | 28% | 27% | 8% | 7% | 8% | 7% |
| 2-Ethoxy-ethanol | — | — | 20% | 20% | — | — | 40% | 40% |
| Water | 5% | 5% | 5% | 5% | 5% | 5% | 5% | 5% |
| Part B | | | | | | | | |
| 2-Propanol | 20% | 20% | — | — | 40% | 40% | — | — |
| Fragrance | 42% | 42% | 42% | 42% | 42% | 42% | 42% | 42% |
| Melting Range (°F.) | | | | | | | | |
| From | 113° | 129° | 110° | 125° | 140° | 140° | 131° | 132° |
| To | 115° | 132° | 111° | 127° | 147° | 142° | 135° | 136° |

$^a$Percent by weight
$^b$The gels were prepared in a manner similar to Examples 1 and 2.

EXAMPLE 6

Carrageenan Gel

| Component | Percent by Weight |
|---|---|
| Water | 75% |
| 2-(2-Ethoxyethoxy)ethanol | 12% |
| Carrageenan | 3% |
| Fragrance | 10% |
| | 100% |

This example is included to illustrate a so-called water gel can be made using a gelling agent such as carrageenan. These gels hold less fragrance and the sodium stearate gels are much preferred and last longer.

We claim:

1. A method for deodorizing a urinal or a toilet bowl which comprises placing in said urinal or toilet bowl a solid gel in a manner such that said gel comes in contact with flush water in said urinal or toilet bowl, said gel containing:
   (a) from 2% to 20% of a gelling agent chosen from the group consisting of sodium salts of fatty acids containing ten to twenty carbon atoms, sodium alginate, carboxy methyl cellulose, carrageenan, hydroxypropyl cellulose, starches and gums;
   (b) from 30% to 80% of an organic solvent chosen from the group consisting of alkyl alcohols having one to six carbon atoms, alkyl diols having two to seven carbon atoms and alkyl ether alcohols having three to eight carbon atoms which have one hydroxyl group and one or two ether linkages;
   (c) from 2% to 10% of water; and,
   (d) from 1% to 55% of a fragrance.

2. A method according to claim 1 wherein said gel contains:
   (a) from 3% to 10% of said gelling agent,
   (b) from 40% to 80% of said solvent,
   (c) from 5% to 10% of said water, and
   (d) from 10% to 40% of said fragrance.

3. A method according to claims 1 or 2 wherein the gelling agent is sodium stearate.

4. A method according to claim 3 wherein the gel has a melting temperature between 130° F. to 200° F.

5. A method according to claim 4 wherein the solvent is chosen from the group consisting of methanol, ethanol, 1-propanol, 2-propanol, butanol, pentanol, ethylene glycol, propylene glycol, hexylene glycol, di-1,2-propylene glycol, 2-methoxyethanol, 2-ethoxyethanol, 2-butoxyethanol, 2-(2-methoxyethoxy)ethanol, 2-(2-ethoxyethoxy)ethanol and 2-(2-butoxyethoxy)ethanol or mixtures thereof.

6. A method according to claim 5 wherein the solvent used is chosen from the group consisting of 2-propanol, 2-(2-ethoxyethoxy)ethanol, 2-ethoxyethanol, hexylene glycol or mixtures thereof.

7. A method according to claim 6 wherein the amount of gel used is between twenty-five grams and seventy-five grams.

* * * * *